(12) United States Patent
Danzer et al.

(10) Patent No.: US 7,358,501 B2
(45) Date of Patent: Apr. 15, 2008

(54) DETECTOR MODULE, DETECTOR AND COMPUTER TOMOGRAPH

(75) Inventors: Ludwig Danzer, Wendelstein (DE); Andreas Freund, Heroldsbach (DE); Björn Heismann, Erlangen (DE); Peter Kämmerer, Schnaittach (DE); Harald Märkl, Gerhardshofen (DE); Claus Pohan, Baiersdorf (DE); Thomas Reichel, Heroldsbach (DE); Gottfried Tschöpa, Rednitzhembach (DE); Stefan Wirth, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 70 days.

(21) Appl. No.: 11/391,399

(22) Filed: Mar. 29, 2006

(65) Prior Publication Data

US 2006/0231767 A1    Oct. 19, 2006

(30) Foreign Application Priority Data

Mar. 29, 2005   (DE) ...................... 10 2005 014 187

(51) Int. Cl.
*G01T 1/24*   (2006.01)

(52) U.S. Cl. .............................................. 250/370.11
(58) Field of Classification Search ............. 250/336.1, 250/370.01, 370.11; 378/19
See application file for complete search history.

(56) References Cited

U.S. PATENT DOCUMENTS

| | | |
|---|---|---|
| 6,396,898 B1 | 5/2002 | Saito et al. |
| 6,510,195 B1 * | 1/2003 | Chappo et al. ............... 378/19 |
| 2003/0010924 A1 * | 1/2003 | El-Hanany et al. .... 250/370.09 |
| 2005/0029463 A1 | 2/2005 | Kaemmerer |

* cited by examiner

*Primary Examiner*—David Porta
*Assistant Examiner*—Mark R Gaworecki
(74) *Attorney, Agent, or Firm*—Harness, Dickey & Pierce, P.L.C.

(57) ABSTRACT

A detector module is disclosed, having an array of detector elements and a printed circuit board. The printed circuit board includes a first region for holding the array of detector elements and includes at least one second region, angled off relative to the first region. On this at least one second region, signal-processing electronics may be arranged. The vertical design of the detector module allows the design of an area detector to be produced on the basis of a multiplicity of detector modules arranged next to one another. The area detector may be provided for a computer tomograph.

23 Claims, 4 Drawing Sheets

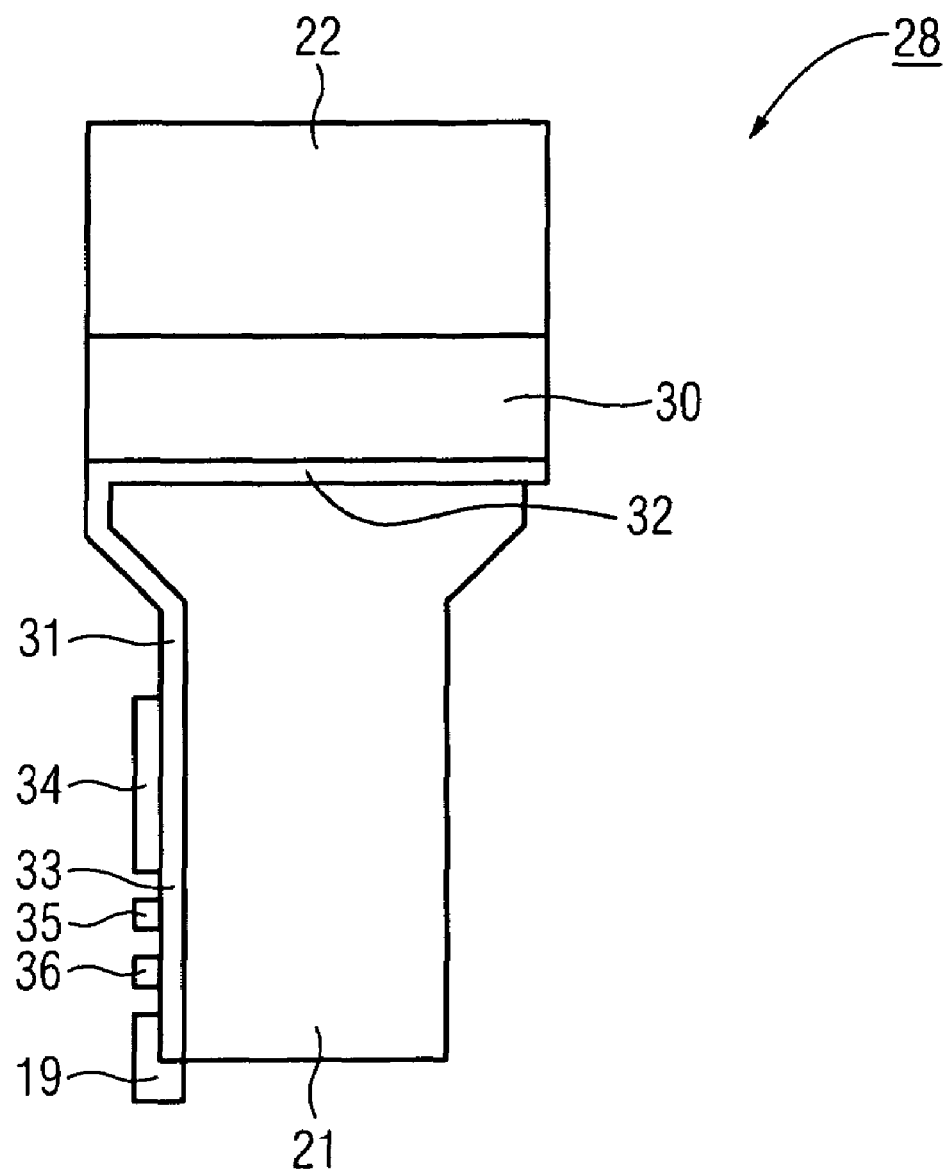

DETECTOR MODULE, DETECTOR AND COMPUTER TOMOGRAPH

The present application hereby claims priority under 35 U.S.C. §119 on German patent application number DE 10 2005 014 187.0 filed Mar. 29, 2005, the entire contents of which is hereby incorporated herein by reference.

FIELD

The invention generally relates to a detector module, having an array of detector elements and a printed circuit board. The invention also generally relates to a detector and a computer tomograph which have a detector module of this type.

BACKGROUND

The aim in imaging using an X-ray machine, e.g. using a computer tomograph, which has an X-ray system with an X-ray source and an X-ray detector, is to make the detection area of the X-ray detector which is available for providing images as large as possible in order to be able to scan entire organs, such as the heart, of a patient in one pass of the X-ray system around the patient, for example. Such an X-ray detector, also called area detector, is normally designed from a multiplicity of detector modules which are lined up in two dimensions.

By way of example, each detector module has a scintillator array and a photodiode array which are oriented relative to one another and which form the detector elements of the detector module. The elements of the scintillator array convert X-ray radiation hitting them into visible light, which is converted into electrical signals by the downstream photodiodes of the photodiode array. A particular problem found with the design of an area detector is the electrical contact for the photodiodes of the detector modules.

In an X-ray detector of conventional design, in which individual detector modules are arranged successively on an arc of a circle, signal-processing electronics can be arranged at the side or a cable used to make contact with the photodiodes of a module can be routed away at the side to a printed circuit board having signal-processing electronics, as can be found in US 2005/0029463 A1, this design is no longer possible for an area detector, since the two-dimensional arrangement of the detector modules means that there is no longer any free space at the sides. It should also be noted in this context that the signal-processing electronics for the measurement signals delivered by the detector elements of the detector modules, which electronics need to be arranged as close as possible to the detector elements for measurement reasons, have an area requirement which may be two to four times greater than the detection area of an actual detector module. For this reason, it appears necessary for the detector module with the signal-processing electronics to be of vertical design.

U.S. Pat. No. 6,396,898 B1 describes the design of an area detector which has a plurality of lined-up detector modules which each comprise an "element block". The element blocks in a detector are of vertical design, i.e. the components of an element block, comprising scintillators, photodiodes, a substrate with signal-processing electronics and a module baseplate, are arranged vertically above one another.

With such a vertical design for a detector module, it is also necessary to ensure good heat dissipation, since otherwise the considerable heat generation during operation of the signal-processing electronics can cause damage to the electronics.

SUMMARY

At least one embodiment of the invention is therefore based on an object of producing a detector module such that it allows the design of an area detector and that sufficient space is present for the arrangement of signal-processing electronics close to the detection area. A further object is to specify a detector designed from such detector modules and a computer tomograph which includes such a detector.

In accordance with at least one embodiment of the invention, the object relating to the detector module is achieved by a detector module, having an array of detector elements and a printed circuit board, where the printed circuit board includes a first region for holding the array of detector elements and comprises at least one second region which is angled off relative to the first region.

In accordance with one variant of at least one embodiment of the invention, there is provision here for the signal-processing electronics, in the form of electronic or electrical components, associated with the array of detector elements to be arranged on the second printed circuit board region, which is angled off relative to the first. The angle between the first and second regions of the printed circuit board is preferably 90° or else somewhat less. This achieves a vertical arrangement for the array of detector elements and of signal-processing electronics arranged below them on the second angled-off region of the printed circuit board.

The array of detector elements and the printed circuit board may have dimensions which are such that, in a plan view of the detector module, the printed circuit board provided with signal-processing electronics does not protrude on any side of the square or rectangular detector module. Accordingly, detector modules of such design can easily be arranged relative to one another in two dimensions, with a slight interspace between the detector modules, to form an area detector.

In accordance with variants of at least one embodiment of the invention, the printed circuit board is in essentially L-shaped form or U-shaped form. When the printed circuit board is in L-shaped form, the array of detector elements is arranged on one limb and the signal-processing electronics are arranged on the other limb of the L-shaped printed circuit board, as already indicated above. When the printed circuit board is in U-shaped form, the array of detector elements may be arranged on that portion of the U-shaped printed circuit board which connects the two limbs, while the two limbs of the U-shaped printed circuit board provide areas for arranging signal-processing electronics.

In accordance with one embodiment of the invention, the printed circuit board can have electrical contact made with it by means of at least one connector or a cable. The connector or the cable connection is preferably located at the end of that limb of the L-shaped or U-printed circuit board which is carrying the signal-processing electronics. In this respect, in continuation of the vertical design of the detector module, a cable, for example, can thus be routed away from the detector module vertically or downward, so that the measurement signals which come from the detector elements of the detector module and which are pre-processed using the signal-processing electronics can be supplied to a computer for further signal processing.

In accordance with a further variant of at least one embodiment of the invention, the printed circuit board may be of integral design. Commercially available, at least partially flexible printed circuit boards can then easily be put into the desired L or U shape, for example.

In accordance with one embodiment of the invention, the detector module has a carrier for the printed circuit board. In this case, the printed circuit board may match the shape of the carrier or the carrier may match the shape of the printed circuit board. The carrier is used for fixing and stabilizing the printed circuit board. In addition, the carrier has a positive effect with regard to electromagnetic interference and at least partially absorbs the X-ray component which has passed through the array of detector elements and which is harmful to the signal-processing electronics.

In accordance with variants of at least one embodiment of the invention, the carrier is made from a material which is a good conductor of heat, preferably from a metal, a ceramic or from a fiberglass reinforced plastic. When the printed circuit board is fixed on the carrier over its area, e.g. using screw connections or bonding, the carrier advantageously also serves to dissipate heat generated during operation of the signal-processing electronics, and therefore prevents the electronics from overheating and becoming damaged.

In accordance with one variant of at least one embodiment of the invention, the array of detector elements is an array of detector elements which directly convert X-ray radiation. Alternatively, the array of detector elements may include a scintillator array and a photodiode array which are oriented relative to one another.

In addition, in accordance with one embodiment of the invention, a collimator is arranged above the array of detector elements, so that the detector elements of a detector module detect only the X-ray radiation from a particular solid angle.

The object relating to the detector is achieved by a detector for X-ray radiation which has a plurality of detector modules of the type described above arranged in two dimensions next to one another. If the detector is provided for a computer tomograph, the detector modules are preferably arranged on a partial cylindrical area in order to form the area detector.

BRIEF DESCRIPTION OF THE DRAWINGS

An example embodiment of the invention is shown in the appended schematic drawings, in which:

FIG. 5 shows a side view of a further detector module based on an embodiment of the invention.

DETAILED DESCRIPTION OF THE EXAMPLE EMBODIMENTS

Figure 1:
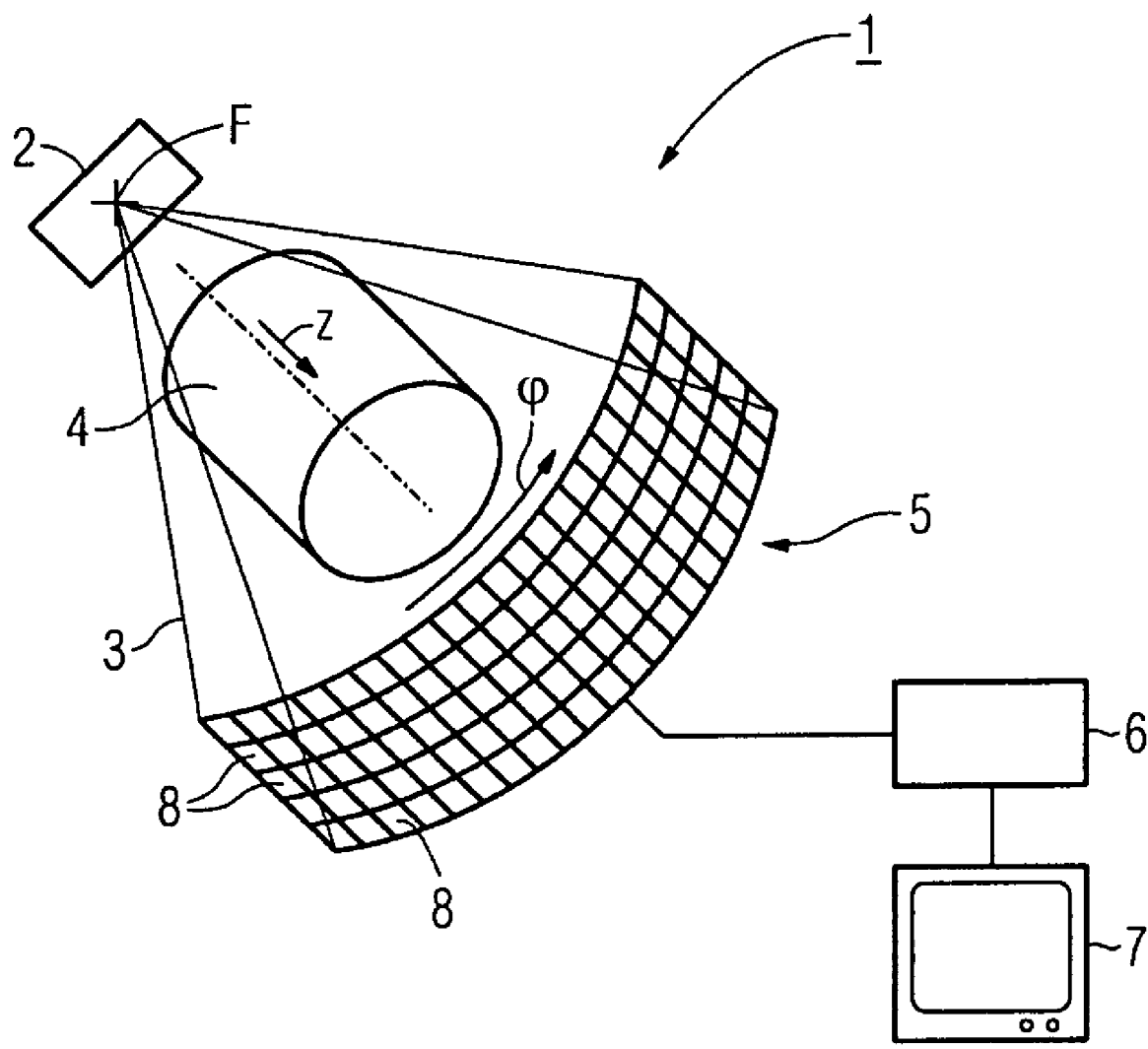
FIG. 1 shows a schematic illustration, partly in the form of a block diagram, of a computer tomograph.

FIG. 1 shows a schematic illustration, partly in the form of a block diagram, of a computer tomograph 1. The computer tomograph 1 includes an X-ray source 2 whose focus F emits an X-ray beam 3 which is shaped by means of screens (which are not shown in FIG. 1 but are known per se), for example in a fan or pyramid shape. The X-ray beam 3 penetrates an examination object 4 which is to be examined and hits an X-ray detector 5. The X-ray source 2 and the X-ray detector 5 are arranged opposite one another (not shown in FIG. 1) on a rotating frame in the computer tomograph 1, which rotating frame can rotate in the $\phi$ direction about the system axis Z of the computer tomograph 1.

During operation of the computer tomograph 1, the X-ray source 2 and the X-ray detector 5, which are arranged on the rotating frame, rotate about the examination object 4, with X-ray shots of the examination object 4 being obtained from different projection directions. In this case, for each projection, X-ray radiation which has passed through the examination object 4 and has been attenuated by the passage through the examination object 4 hits the X-ray detector 5, and the X-ray detector 5 produces signals which correspond to the intensity of the X-ray radiation which has hit. From the signals ascertained by means of the X-ray detector 5, an image computer 6 then calculates one or more two-dimensional or three-dimensional images of the examination object 4 in a manner which is known per se, and these can be displayed on a visual display unit 7.

In the case of the present example embodiment, the X-ray detector 5 has a multiplicity of detector modules 8 which are arranged in the $\phi$ direction and in the Z direction next to one another on a partial cylindrical area and form the two-dimensional X-ray detector 5.

Figure 2:
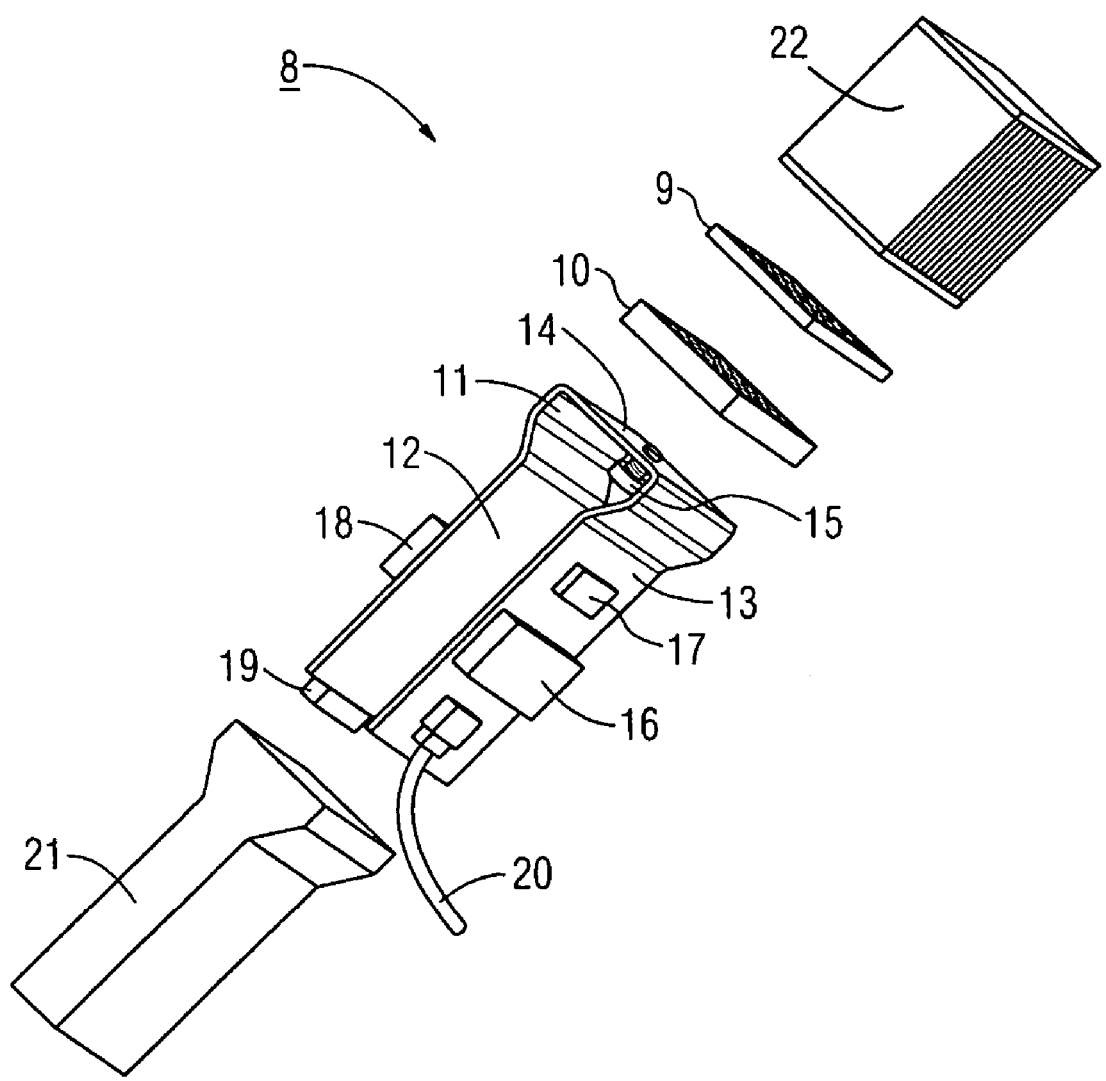
FIG. 2 shows an exploded, perspective illustration of a detector module based on an embodiment of the invention.

A detector module 8 in the X-ray detector 5 is shown in an exploded illustration in FIG. 2. The detector module 8 has a vertical design, with a scintillator array 9 being arranged above a photodiode array 10. The scintillator array 9 is structured and accordingly includes a multiplicity of scintillator elements (not shown in more detail) which are respectively associated with a photodiode in the photodiode array 10, which includes a multiplicity of photodiodes. The scintillator array 9 and the photodiode array 10 are oriented relative to one another and are bonded to one another.

The scintillator array 9 and the photodiode array thus form an array of detector elements for X-ray radiation, where a detector element has a scintillator element and a photodiode. The photodiode array 10 is arranged on a printed circuit board 11, which is in U-shaped form in the case of the present example embodiment and which has integrated (in a manner which is not shown in more detail in FIG. 2) conductor tracks for supplying power and routing signals. The photodiode array 10 is mounted detachably, i.e. interchangeably, on the portion 14 of the U-shaped printed circuit board 11 which connects the two limbs 12 and 13, has electrical contact made with it by means of the conductor tracks on the printed circuit board 11, and may have additional protection so that unwanted separation of the photodiode array from the printed circuit board 11 does not occur during operation of the computer tomograph 1, when the X-ray detector 5 is rotating at high speed about the system axis Z.

The protection may be provided by way of a locking screw 15, for example, as indicated in FIG. 2. Other protective devices, for example retaining clamps, clips or the like, may also be provided, however. Alternatively, the photodiode array 10 may also be soldered onto the portion 14 such that the conductor tracks on the printed circuit board 11 have contact made with them by the photodiode array 10.

Electronic components 16, 17, 18 are arranged on the printed circuit board 11 for signal preprocessing for measurement signals obtained using the array of detector elements. By way of example, these are electronic components or circuits for voltage conditioning, for decoupling noise signals, for preamplification and for analog-digital conversion. In addition, one or more ASICs may be provided for signal processing.

The preferably integrally designed printed circuit board 11 can have electrical contact made with it via a connector 19 arranged at the end of the limb 12 or else via a connecting cable 20 soldered onto the end of the limb 13. The printed circuit board 11 is therefore supplied with a supply voltage and a supply current via a cable which can be connected to the connector 19 and/or via the cable 20. In addition, the connector 19 and/or the cable 20 are used to route the preferably digitized measurement signals away from the printed circuit board 11. In this case, the measurement signals are routed to the image computer 6 via an interface (not shown) between the rotating portion of the computer tomograph 1 and the fixed portion of the computer tomograph 1, which interface is slip rings, for example.

As can also be seen from FIG. 2, the printed circuit board 11 has an associated carrier 21. In the case of the present example embodiment, the printed circuit board 11 matches the shape of the carrier 21 by virtue of the printed circuit board being as good as folded around the carrier 21. In this case, the printed circuit board 11, in U-shaped or clamp-like form, is in contact with the carrier 21 over as large an area as possible, which is produced by areal pressure, for example by way of a screw connection (not shown in more detail).

The carrier 21, which may be made from a metal, a ceramic or from a fiberglass reinforced plastic for example, is not only used to stabilize and fix the printed circuit board 11 but also ensures that the heat generated by the electronic components 16 to 18 arranged on the printed circuit board 11 during operation of the detector module is dissipated. For this reason, the carrier 21 is made from a material which is a good conductor of heat. In addition, the carrier 21 is found to be advantageous inasmuch as it at least partly absorbs the X-ray radiation which has passed through the scintillator array 9 and the photodiode array 10 in unwanted fashion and which is harmful to the electronics arranged on the printed circuit board 11.

As can also be seen from FIG. 2, the detector module 8 also has a collimator 22 which is arranged in defined fashion above the scintillator array 9. In this way, the scintillator array 9 is hit only by X-ray radiation from a particular solid angle, which is achieved by the collimator plates 23 (shown in more detail in FIG. 4) of the collimator 22.

Figure 3:
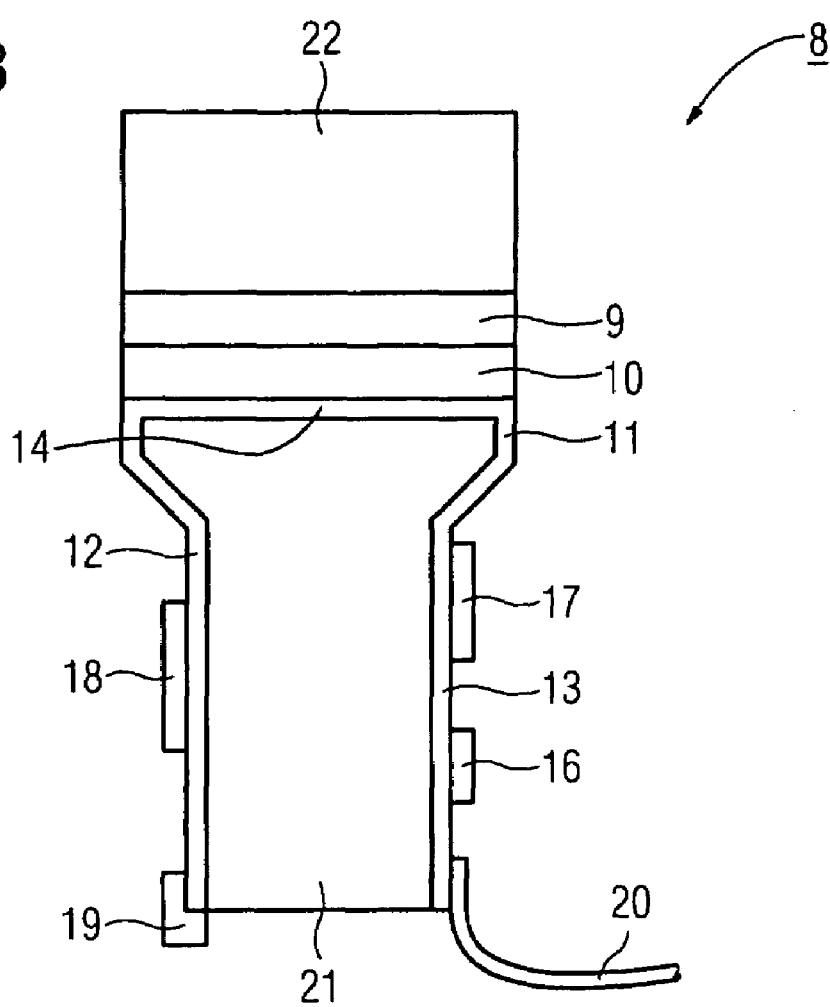
FIG. 3 shows a side view of the detector module from FIG. 2.
Figure 4:
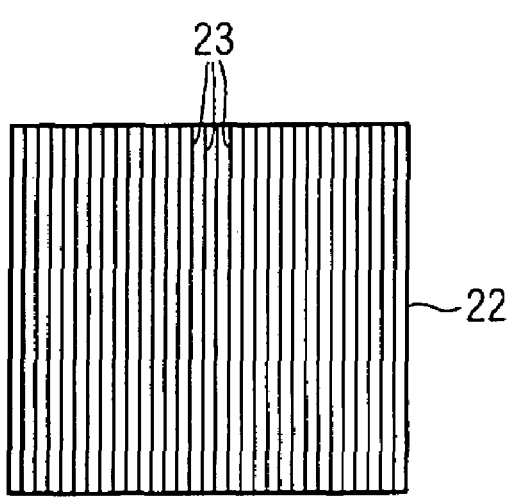
FIG. 4 shows a plan view of the detector module from FIG. 3.

FIG. 3 shows the detector module 8 again in a side view in the assembled state. As can be seen in FIG. 4, in particular, which is a plan view of the detector module 8 from FIG. 3, the design of the detector module 8 is such that no component of the detector module 8, particularly not the printed circuit board 11 provided with the electronics, protrudes at the sides in a plan view of the detector module 8. On account of the inventive design, it is therefore possible to arrange the detector modules 8, as indicated schematically in FIG. 1, next to one another in two dimensions in the Z and ϕ directions such that a large-area detector in the form of the X-ray detector 5 can be built. In this case, a partial cylindrical area has had the detector modules 8 fitted to it.

The inventive vertical design of the detector module 8 of at least one embodiment additionally also allows stable operation of the detector, a particularly advantageous effect being that the stabilizing carrier 21 routes the heat generated by the electronic components away from the printed circuit board 11. To this end, the carrier 21 may also be connected to further lines or apparatuses for dissipating the heat (not shown in more detail).

Hence, when, during operation of the computer tomograph 1, X-ray radiation which has passed through the examination object 4 and has been attenuated hits the scintillator array 9 through the collimator 22, the individual scintillator elements in the scintillator array 9 convert the X-ray radiation into visible light, which is in turn converted into electrical signals by the photodiodes in the photodiode array 10, and these signals are conditioned by the electronic components present on the printed circuit board 11 and are passed to the image computer 6 for further signal processing. As already mentioned, the image computer 6 can be used to reconstruct images of the examination object 4 from the X-ray shots obtained at various projection angles.

FIG. 5 shows an alternative design of a detector module 28 based on at least one embodiment of the invention, where components of the detector module 28 which essentially correspond to the components of the detector module 8 in terms of their design and their function have been provided with the same reference symbols.

The detector module 28 shown in FIG. 5 differs from the detector module 8 shown in FIG. 3 essentially in that the array of detector elements is an array 30 of detector elements which directly convert X-ray radiation. This is an array of detector elements from an inherently known semiconductor material which is able to convert impinging X-ray radiation directly into electrical signals. Another difference from the detector module 8 from FIG. 3 is the L-shaped design of the printed circuit board 31. The L-shaped printed circuit board 31 has a limb 32, on which the array 30 of detector elements directly converting X-ray radiation is arranged, and a limb 33, on which electronic components 34 to 36 are arranged and which is provided with the connector 19.

In terms of function, the components 34 to 36 and the connector 19 do not differ from the corresponding components shown in FIG. 3. The printed circuit board 31 is again arranged on a carrier 21 which is preferably made from a metal, a ceramic or from a fiberglass reinforced plastic and which is used for stabilization, fixing and for dissipating the heat generated by the electronic components 34 to 36 during operation. A large-area X-ray detector can therefore also be designed using the detector module shown in FIG. 5.

It goes without saying that the invention permits combinations of various components in the detector modules shown in FIGS. 3 and 5 in any form.

When the text above mentions that the printed circuit board is in U-shaped or L-shaped form, this does not mean that the printed circuit board must have an exact L shape or U shape. Rather, as can be seen from FIGS. 3 and 5, in particular, the shape of the printed circuit board may be only essentially L-shaped or U-shaped and may possibly have its function modified, but while retaining the shape, such that the limbs of the printed circuit board are slightly inward, so that the electronic components are prevented from protruding from the detector module at the sides in an arrangement of electronic components on the printed circuit board. This has the particular advantage that, apart from circuits designed specifically for signal processing, commercially available standard components from electrical engineering can be used.

In addition, the electronic components may also be arranged on the printed circuit board's inside facing the carrier. In this case, the carrier has one or more corresponding cutouts, possibly matching the respective component.

In addition, the printed circuit board must not necessarily be L-shaped or U-shaped, but rather may also be in square form or in another form within the scope of the invention. A fundamental feature is that the printed circuit board comprises at least one second region which is angled off relative to a first region, in order to allow the vertical design of the detector module.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector module, comprising:
   an array of detector elements for detecting X-ray radiation;
   a printed circuit board including a first region for holding the array of detector elements and at least one second region; and
   a carrier for fixing and stabilizing the printed circuit board, wherein
   the at least one second region is angled off relative to the first region and protruding away from both the first region and the array of detector elements, wherein
   the first region and the at least second region are in contact with the carrier over as large an area as possible, and wherein
   the carrier is made of at least one of a metal, a ceramic, and a fiberglass reinforced plastic.

2. The detector module as claimed in claim 1, wherein at least one electronic component for signal processing is arranged on the at least one second region of the printed circuit board.

3. The detector module as claimed in claim 2, wherein the printed circuit board is in at least one of essentially L-shaped form and essentially U-shaped form.

4. The detector module as claimed in claim 3, wherein the array is arranged on a limb of the essentially L-shaped circuit board.

5. The detector module as claimed in claim 3, wherein the array is arranged on that portion of the essentially U-shaped printed circuit board which connects the two limbs.

6. A detector for X-ray radiation having a plurality of detector modules as claimed in claim 2.

7. A computer tomograph having a detector as claimed in claim 6.

8. The detector module as claimed in claim 1, wherein the printed circuit board is in at least one of essentially L-shaped form and essentially U-shaped form.

9. The detector module as claimed in claim 8, wherein the array is arranged on a limb of the essentially L-shaped circuit board.

10. The detector module as claimed in claim 8, wherein the array is arranged on that portion of the essentially U-shaped printed circuit board which connects the two limbs.

11. The detector module as claimed in claim 1, wherein the printed circuit board is electrically contactable via at least one of at least one connector and a cable.

12. The detector module as claimed in claim 1, wherein the printed circuit board is of integral design.

13. The detector module as claimed in claim 1, wherein the array of detector elements is an array of detector elements which directly convert X-ray radiation.

14. The detector module as claimed in claim 1, wherein the array of detector elements has a scintillator array and a photodiode array.

15. The detector module as claimed in claim 1, comprising a collimator arranged above the array of detector elements.

16. A detector for X-ray radiation having a plurality of detector modules as claimed in claim 1.

17. The detector as claimed in claim 16, wherein the detector modules are in a two-dimensional arrangement.

18. A detector as claimed in claim 17, wherein the detector modules are arranged on a partial cylindrical area.

19. A computer tomograph having a detector as claimed in claim 18.

20. A computer tomograph having a detector as claimed in claim 17.

21. A detector as claimed in claim 16, wherein the detector modules are arranged on a partial cylindrical area.

22. A computer tomograph having a detector as claimed in claim 21.

23. A computer tomograph having a detector as claimed in claim 16.

* * * * *